United States Patent [19]

Andersson

[11] Patent Number: 5,059,758

[45] Date of Patent: Oct. 22, 1991

[54] METHOD AND AN APPARATUS FOR JOINING TOGETHER TWO ELEMENTS INCLUDED IN AN IMPLANT AND/OR PROSTHESIS STRUCTURE

[75] Inventor: Matts Andersson, Karlskoga, Sweden

[73] Assignee: Nobelpharma AB, Gothenburg, Sweden

[21] Appl. No.: 344,570

[22] Filed: Apr. 28, 1989

[30] Foreign Application Priority Data

Apr. 28, 1988 [SE] Sweden .................................. 8801601

[51] Int. Cl.⁵ .............................................. B23K 26/00
[52] U.S. Cl. ............................ 219/121.63; 219/121.64
[58] Field of Search ....................... 219/121.63, 121.64

[56] References Cited

U.S. PATENT DOCUMENTS

| | | | |
|---|---|---|---|
| 4,708,654 | 11/1987 | Branemark | 433/213 |
| 4,714,815 | 12/1987 | Swarts et al. | 219/121.63 |
| 4,767,328 | 8/1988 | Branemark | 433/168.1 |

FOREIGN PATENT DOCUMENTS

| | | |
|---|---|---|
| WO86/00217 | 1/1986 | PCT Int'l Appl. . |
| WO86/00218 | 1/1986 | PCT Int'l Appl. . |
| 448600 | 3/1987 | Sweden . |

Primary Examiner—C. L. Albritton
Attorney, Agent, or Firm—Pollock, Vande Sande & Priddy

[57] ABSTRACT

In the joining of two elements of hard material which are included in an implant or prosthetic structure, the elements are disposed towards one another by means of a joint formed by contact surfaces. The elements are adjusted to one another and mutually fixed and welded together by laser equipment. Registering circumferential portions of the joint are exposed to two focusing optical devices which emit laser pulses for the welding and form a part of the laser equipment. The focusing devices are aligned each towards one of two substantially registering, or slightly mutually offset, starting areas. Each respective area includes a section of each respective joint circumferential portion with circumjacent parts on the elements. The laser equipment is energized to emit, through the focusing devices, simultaneous or alternating laser pulses or laser beams, and the elements and devices are mutually, controllably displaceable such that laser output emission may be effected towards the starting areas and subsequent areas with associated sections of joint circumferential portions and material parts.

19 Claims, 1 Drawing Sheet

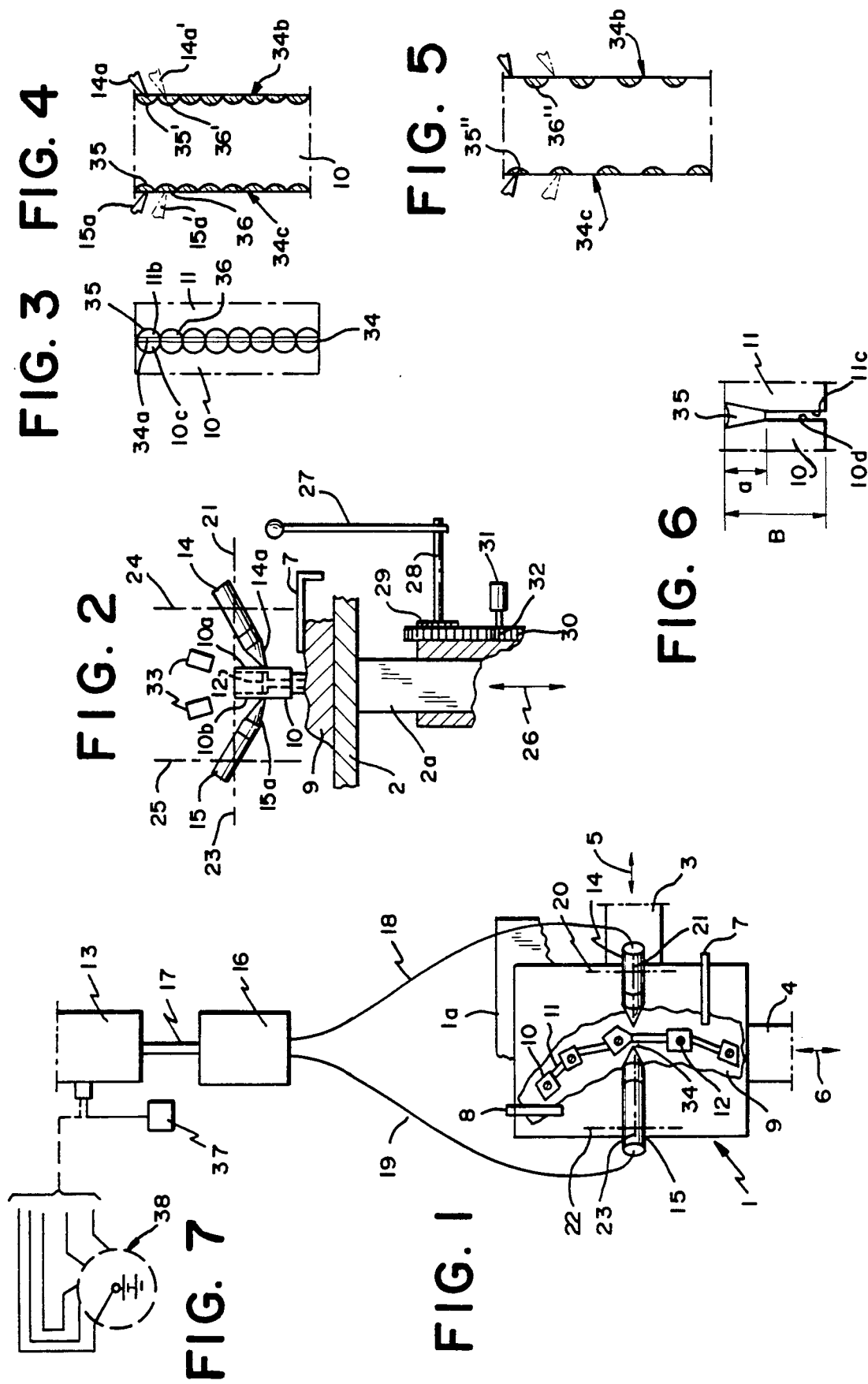

5,059,758

METHOD AND AN APPARATUS FOR JOINING TOGETHER TWO ELEMENTS INCLUDED IN AN IMPLANT AND/OR PROSTHESIS STRUCTURE

TECHNICAL FIELD

The present invention relates to a method of joining together, at least substantially, distortion-free, two elements of hard material, preferably of titanium, and included in a structure for implants and/or prostheses. Examples of structures of the type contemplated here are dental prosthetic bridges, dental crown arrangements, joint components, other prosthetic parts, and the like. The process comprises a first part process in which two reciprocally disposable contact surfaces are accurately registered and fixed to one another via a joint, and a second part process in which the joining together proper takes place by means of welding using laser equipment. The invention also relates to an apparatus for carrying the novel method into effect.

BACKGROUND ART

It is previously known in this art to propose that such joining together could be practicable in purely general terms with the aid of laser welding. It is also known in this art to produce prosthetic structures of the type contemplated here with the aid of prefabricated modular elements which, in a process preceding the welding process, are selected and adapted to one another such that individual form and extent may, in any event, be obtained for the structure in question. This affords advantages in comparison with a case in which the structure is produced in one piece, which involves a complex and expensive production process because of the individual nature of the structure.

In one prior-art process, accurate cutting and adaptation of the contact surfaces are effected. For instance, in conjunction with the production of bridges (dental prosthetic bodies), the requirement of accuracy of fit is high in the extreme. The cutting operation may be performed using a cutting wheel and the surfaces are also worked with grinding or polishing tools which give a high-quality finish at the joints/gaps between the units.

In the prior-art process, use is made of a positive working model of a relevant dental impression. The model is designed with anchorage means for the modular elements and the anchorage means correspond with extreme accuracy in their positioning and extent to the actual positions of the anchorage means (pins) implanted in the patient's mouth.

SUMMARY OF THE INVENTION

Technical Problem

In the production of prosthetic structures and implant structures, in particular these employed in artificial dental constructions, it is an absolute requirement that the high degree of accuracy be retained throughout the entire production process which must be feasible with an accuracy of one or a few hundredths of a millimetre. An unacceptable deviation will result in extreme stress for the patient because retesting and reworking must be carried out.

Joining together by welding of titanium or similar hard materials places extreme demands of accuracy on the process and apparatus employed. It must be possible for production to be carried out by machine and in a rational manner. The welding should not give rise to stresses and distortions in the modular elements (the bridge), which might result in bridges or similar structures changing shape beyond permitted very tiny margins.

SOLUTION

The object of the present invention is a novel process and a novel apparatus resolving the above and other problems.

The novel process according to the present invention is characterized in that the elements are disposed with registering circumferential portions, for instance sides, on the joint exposable to two focusing optical devices which emit laser pulses or laser beams and form part of the laser equipment. At the registering joint circumferential portions, the devices are then each aimed at one of two substantially registering, or slightly mutually, offset starting areas which each include their section of each respective joint circumferential portion with circumjacent material parts on the elements. The laser equipment is energized to emit, via the devices, the laser pulses or laser beams while the elements and devices are mutually influenced for attaining laser power emission towards the starting areas and the subsequent areas with associated sections of the joint circumferential portions and material parts. In such instance, the devices may be operative to emit their laser pulses or laser beams simultaneously or alternatingly.

In one embodiment, the elements are secured and fixed with the contact surfaces in abutment against one another in a positive model which is utilized as a fixing tool. The model is secured on an adjustable, for example vertically adjustable, surface which, on laser power emission, is actuated in relation to the focusing optical devices which, in this instance, are disposed (fixedly clamped) in relation to the surface. The mutual control between the elements and the devices is preferably carried out under simultaneous ocular scanning of the elements, joints and devices. The mutual movements between the elements and devices are controlled such that the devices are first aimed towards a relevant area and, thereafter, the laser pulses for the welding operation are emitted. Alternatively, zig-zag spot welding may be carried out and after movement to a new area, welding takes place only on the one side and, on advancement to a subsequent area, welding takes place only on the other side, and so on. Alternatively, welding may be effected first with one device and then with the other device before mutual movement takes place between the elements and the devices.

The novel apparatus according to the present invention is characterized, in that, among other things two focusing optical devices are disposed to be alignable each from their side towards registering circumferential portions (sides) of the joint when the elements, in the adapted and fixed state, are applied to an application substrate. The focusing optical devices and application substrate are mutually displaceably controllable so that the focusing devices are first alignable towards two substantially registering, or slightly mutually offset starting areas which each include their section of each respective joint circumferential portion with circumjacent material parts on the elements, and thereafter are stepwise or continually alignable towards areas subsequent to the starting areas and with associated sections of joint circumferential portions and material parts. The laser equipment is disposed, in conjunction with the displacement control, to emit operational laser pulses or laser beams.

According to one preferred embodiment, the focusing optical devices are fixedly disposed in relation to the application substrate, which, in its turn, is controllable in relation to the devices in one or more directions, for example in the vertical direction. The apparatus is preferably of the type which includes magnification devices by means of which the alignment towards the different areas is controllable, at the same time as the joint and the welding process proper may be monitored.

Advancement to the different welding points or areas may be carried out stepwise and the laser pulse emission may be effected after each respective advancement step. In such instance, the laser pulse emission may be performed simultaneously from the focusing optical devices. Alternatively, zig-zag spot welding may be carried out, i.e. the first device is activated to emit laser pulses every second time and the second focusing optical device is activated to emit laser pulses every second time, in which event the welding spots at both sides (or their equivalent) of the joint will be offset one step. As an alternative to the laser pulse emission, continuous laser beam emission may be effected.

ADVANTAGES

Employment of the method and the apparatus according to the present invention will provide essentially distortion-free implant structures or prosthetic structures of titanium and similar hard material. Production may be rendered both rationally and economically, despite the highly divergent individual designs of the structures.

BRIEF DESCRIPTION OF THE ACCOMPANYING DRAWINGS

The nature of the present invention and its aspects will be more readily understood from the following brief description of the accompanying Drawings, and the discussion relating thereto.

In the accompanying Drawings:

FIG. 1 is a horizontal view fundamentally illustrating equipment for laser welding of modular elements applied to a working model which is disposed on a work table and in which focusing optical devices are provided for making possible welding of both sides of a joint, the devices being connected to a laser source;

FIG. 2 shows, in vertical section, parts of the equipment according to FIG. 1;

FIG. 3 is a side elevation, on a larger scale in relation to FIGS. 1 and 2, showing welding points at a joint between two elements;

FIG. 4 is a cross-section through the joint according to FIG. 3;

FIG. 5 shows one alternative embodiment of the joint according to FIG. 4;

FIG. 6 is a top plan view of an example of a welding joint; and

FIG. 7 schematically illustrates the advancement mechanism for mutual adjustment of the elements and the focusing optical devices.

DESCRIPTION OF PREFERRED EMBODIMENT

Referring to the Drawings, the apparatus according to the invention includes a known machine 1 which is provided with a moving table 2. In the view according to FIG. 1, the table is displaceable along the X and Y axes with the aid of activation means (of the micrometer screw type) 3 and 4, respectively. The directions of activation are indicated by means of arrows 5 and 6, respectively. The table is carried in a machine frame 1a in the known manner.

A positive working model 9 of the known type is secured to the table by means of retention members 7, 8. The working model constitutes a positive copy of a dentine impression. A multiple component bridge is to be produced with the aid of the model and is constructed from prefabricated modular elements 10, 11. The modular elements may vary in number between two or more and may be substantially identical or mutually different.

In the illustrated case, every other modular element 10 is fixedly secured in the known manner in the working model with the aid of retention members 12, for instance in the form of a screw. The screw is screwed in place in retention members in the model 9, these retention members corresponding in their location and extent to implanted pins in the dentine of the patient. In the illustrated embodiment, every other element 11 is in the form of a beam-like element which, through end surfaces, may be fixedly welded in the first-mentioned modular element 10.

The equipment according to FIG. 1 also includes known laser welding equipment with a laser source 13 and with focusing optical devices 14, 15 which are connected to a radiation distributor 16 which, in turn, is connected to the laser source 13 by means of a connection 17. The connection between the radiation distributor and the devices comprises optical fibres 18 and 19 which, hence, are flexible. In the present case, two devices 14 and 15 are employed. Indeed, it is possible to employ a greater number of devices connected to the unit 16 in a corresponding manner. Alternatively, two laser sources 13 may be employed, each being provided with its own focusing optical device. Preferably, such focusing optical devices and connections 18, 19 are employed to provide for high power transmission with a relatively slight cross-sectional area of the optic fiber. Fiber optic devices with such connections 18 or 19 are readily available on the market. As an alternative to such fiber connections, use may be made of jointed optical connections (rigid conductive sections connected at articulated points).

The devices are anchorably disposed in connection with the machine 1. The anchorage may be fixedly secured with the aid of known jigs and locking means (screws). In FIG. 1, these jigs are schematically indicated by reference numerals 20, 21; and 22, 23.

FIG. 2 shows the equipment according to FIG. 1 in vertical section. The devices 14, 15 may also be vertically adjusted, the jigs in this case being indicated by reference numerals 24, 25. By the locking arrangement for the devices 14, 15, these may be fixedly disposed in relation to the table 2 which, according to FIG. 2, is also adjustable in the vertical direction 26. The retention devices 7, 8 may consist of clamps or the like. In FIG. 2, the retention device 7 has been partly eliminated for purposes of clarity.

Vertical control may be effected in the known manner with the aid of a lever 27 for manual activation. A shaft 28 is fixedly secured to the lever, and a gearwheel 29, partly concealed in FIG. 2, is non-rotatably disposed thereon and engages with a gear rack 30. The latter is fixedly disposed on a column 2a of the table 2. When the lever is activated, the table 2 will thus move in the vertical direction. Alternatively, vertical directional control of the table 2 may be effected by means of a stepping motor 31, on whose output shaft there is disposed a gearwheel which is in engagement with the gear rack 30.

The equipment 1 shown in FIG. 1 may also be provided, in the known manner, with magnification devices which, in FIG. 2, are represented by their optical portions 33. According to the illustrated embodiment, the elements 10, 11 are, thus, displaceably disposed in relation to the devices 14, 15. Naturally, the system may be arranged such that the devices 14, 15 are movable with respect to fixedly disposed elements (the table 2). As a result of the versatile adjustment capability of the devices 14, 15 in their support 21–25, and by a selected clamping position of the model 9 on the table 2, the focusing optical devices may be aligned each towards their side 10a, 10b, respectively of the elements/joints between the elements 10, 11. In FIG. 2, the front ends of the devices have been indicated by reference numerals 14a and 15a respectively. The devices are set so close to the joint 34 (FIG. 1) that an optimum distance for the welding will be obtained at each respective welding point. The case as illustrated in FIGS. 1 and 2 relates to modular elements 10, 11 with vertically extending side surfaces 10a, 10b and joint sides. By such means, optimum welding may be effected along the entire length of the joint, in that the table 2 is activated in the vertical direction while welding is in progress. In that case when the joints/element sides are of different lengths, the mutual movement between the elements and the devices must be controlled correspondingly. It is indeed possible to design the devices with anchorages which make possible adjustments of the devices to non-vertical joints/sides. The basic requirement for the relative guiding between the elements and the devices is that the devices must always assume an optimum distance in relation to the joint.

FIG. 3 is intended to show welding points or "spots" along the joint. The points or spots form regions or areas which each encompass a joint side portion and circumjacent material on the elements 10, 11. In FIG. 3, the starting area is shown by reference numeral 35. The starting area encompasses a joint side portion 34a and material regions 10c and 11b respectively. The region 35, which may also be considered as representing the starting spot from the device 14, 15 in question, should in principle be as small as possible such that the departing light beam from the device should be of high concentration. Fundamentally, the welding operation proceeds such that each respective device is aimed at a starting area which may consist of the area 35. Laser pulse emission then takes place against the aligned portion, which entails that a welding point occur. Thereafter, the mutual position between the elements and the devices is influenced such that alignment of the device in question takes place towards a subsequent area 36, with subsequent laser pulse emission, and so on until the entire joint has progressively been spot welded.

According to the present invention, the welding operation is to be effected in coordination on both sides 34b and 34c respectively of the joint. In such instance, the device 14a caters for the welding function on side 34b, while the device 15a caters for the welding on side 34c. In the Figure, the device tips 14a and 15a respectively have been shown as disposed adjacent the areas 35 and 35'. The relative positional change has been indicated by reference numerals 14a' and 15a' respectively, having then been disposed adjacent the areas 36, 36'. In one embodiment, activation of the laser equipment/devices 14, 15 takes place simultaneously, entailing that two welding points located in register with one another will be obtained simultaneously at the joint. Alternatively, the welding point 35 may be welded before welding point 35', or vice versa.

A further alternative is shown in FIG. 5, where only every other region of each respective joint side 34b and 34c respectively has been welded. The different alternatives are dependent upon the amount of energy required at each welding point and the power output of the laser welding equipment available. In that case when it is sufficient to be able to weld using half of the output of the laser source on each respective side, simultaneous welding of each welding point may be effected. In such instance, the output from the laser source 13 is divided up into two parallel paths in the radiation distributor 16, the one path being led via the connection 18 to the device 14, and the other through the connection 19 to the device 23. In that case when greater output is required for each welding point, zig-zag welding may be employed. FIG. 6 shows the depth a of the joint 35. It is essential that the welding joint penetrates deep into the material/the joint. By way of example, it might be mentioned that joint depths of approx. 0.4 mm are desirable in a width B of the elements of, for instance, 2.0 mm. The contact surfaces are indicated by reference numerals 10d and 11c. The modular elements may have other cross-sectional configurations than rectangular or quadratic.

FIG. 7 shows that the impulse emission from the laser equipment/devices 14, 15 may be effected as soon as advancement to a new region 35, 36 has taken place. The advancement mechanism which may be connected to the lever 27 or the motor 31, emits, in each advanced position, a triggering signal to the laser equipment which is activated to emit its impulse in each respective advanced position. Activation of the laser equipment may take place independently of the mutual displacement influenced between the elements and the devices. Alternatively, the laser equipment may be activated by a manual activator 37. The afore-mentioned advancement mechanism is indicated by reference numeral 38.

In one mode of approach according to the present invention, the joint is first prepared by being ground in a fixture. In principle, the gap should be 0 or as small as possible. All edges must be sharp. Joints in which the gap at any point exceeds a certain level, for instance 0.1 mm, must be reground so that the requirement of joints which are less than the predetermined value, for example, 0.1 mm, is satisfied. Loose beams are secured to the model using plastic adhesive (not wax). Possibly contaminated welding surfaces must be washed before the welding operation is carried out. The laser parameters are checked before commencement of the welding operation, and this may be effected by welding a test rod in a specifically allocated tool. The rods are designed with smooth-ground end surfaces. The thus executed welding is inspected and any possible adjustment to the laser parameters is then carried out.

Thereafter, the modular elements or the bridge are mounted in the welding fixture (the working model). All joints are inspected through a microscope and/or on a TV monitor connected to the equipment. As in all laser welding, use is also made here of a shielding gas during the welding. In such instance, it is vital to ensure that the shielding gas covers all welding points in a known manner. The welding may thereafter proceed.

The finished bridge is inspected on both sides in the microscope with respect to cracks, porosity, depressions and discoloration. The screws 12 are removed and the fit is checked.

DESCRIPTION OF ALTERNATIVE EMBODIMENT

In one alternative embodiment, continuous or substantially stepless laser radiation welding is employed via each respective device 14 and 15 during the simultaneous mutual guiding of the devices and the elements 10, 11, such guiding being, in this case, continuous.

The present invention should not be considered as restricted to the embodiments described above by way of example, many modifications being conceivable without departing from the spirit and scope of the appended Claims and the inventive concept as herein disclosed.

What we claim and desire to secure by Letters Patent is:

1. A method for a distortion-free joining of at least two elements of hard material, preferably of titanium, included in an implant structure and/or prosthetic structure, comprising the steps of:
    adjusting two registering contact surfaces of the two elements to fit each other with high accuracy and to form a joint therebetween;
    providing means for supporting said mutually adjusted elements in a fixed state;
    positioning at least two focusing optical devices, constituting part of the laser equipment for welding said elements, on the opposite sides of the joint towards the registering circumferential portions of the joint;
    said means for supporting and said optical elements being controllably displaceable;
    effecting alignment of said focusing devices towards two substantially registering, or slightly mutually offset starting areas which each include their section of each respective joint circumferential portion with circumjacent material parts on the elements, and thereafter towards areas subsequent to the starting areas and with associated sections of joint circumferential portions and material parts prior to emission of the laser pulses effecting the welding; and
    delivering the laser pulses for performing the welding.

2. The method as claimed in claim 1, wherein the elements are adapted to one another and fixed with the contact surfaces in abutment against one another in a positive model being fixedly secured to a vertically adjustable substrate constituting said means for supporting which, on laser power emission, is actuated for adjustment with respect to the focusing optical devices which are fixedly disposed in relation to the substrate.

3. The method as claimed in claim 1, wherein the elements and focusing devices are mutually actuated under simultaneous ocular inspection of the elements, joints and focusing devices.

4. The method as claimed in claim 1, wherein the mutual movements between the elements and the focusing devices are guided such that the devices are first aligned towards a relevant area, and thereafter the laser pulses for the welding are emitted.

5. The method as claimed in claim 2, wherein the elements and focusing devices are mutually actuated under simultaneous ocular inspection of the elements, joint and focusing devices.

6. The method as claimed in claim 3, wherein the mutual movements between the elements and the focusing devices are guided such that the focusing devices are first aligned towards a relevant area, and thereafter the laser pulses for the welding are emitted.

7. An apparatus for distortion-free joining, by laser equipment of two elements of hard material, preferably of titanium, included in an implant structure or prosthetic structure, in which the elements display two contact surfaces which are adapted to one another and mutually fixed through a joint having registering circumferential portions, said apparatus comprising:
    means for supporting said mutually adjusted elements in a
    at least two focusing optical devices constituting part of the laser equipment for welding said elements, said optical devices being disposed on the opposite sides of the joint towards the registering circumferential portions of the joint;
    said means for supporting and said optical elements being controllably displaceable for effecting alignment of said focusing devices towards two substantially registering, or slightly mutually offset starting areas which each include their section of each respective joint circumferential portion with circumjacent material parts on the elements, and thereafter towards areas subsequent to the starting areas and with associated sections of joint circumferential portions and material parts prior to emission of the laster pulses effecting the welding.

8. The apparatus as claimed in claim 7, wherein the focusing optical devices are fixedly disposed; and wherein the means for supporting is movable in relation to the focusing devices in at least one direction.

9. The apparatus as claimed in claim 7, further including magnification devices for checking the alignment of said focusing devices towards the different areas.

10. The apparatus as claimed in claim 7, wherein the mutual setting between the different areas is effected stepwise; and wherein the laser output emission is effected after each respective setting.

11. The apparatus as claimed in claim 7, wherein the laser output emission takes place at every other step on each respective side of the joint.

12. The apparatus as claimed in claim 7, wherein the laser output emission and the mutual guiding of each respective focusing device and element take place substantially steplessly or continually on one or both sides of the joint.

13. The apparatus as claimed in claim 8, further including magnification devices, for checking the alignment towards the different areas.

14. The apparatus as claimed in claim 8, wherein the mutual setting between the different areas is effected stepwise; and the laser output emission may be effectuated after each respective setting.

15. The apparatus as claimed in claim 9, wherein the mutual setting between the different areas is effected stepwise; and wherein the laser output emission is effected after each respective setting.

16. The apparatus as claimed in claim 8, wherein the laser output emission takes place at every other step on each respective side of the joint.

17. The apparatus as claimed in claim 10, wherein the laser output emission takes place at every other step on each respective side of the joint.

18. The apparatus as claimed in claim 8, wherein the laser output emission and the mutual guiding of each respective focusing device and element take place substantially steplessly or continually on one or both sides of the joint.

19. The apparatus as claimed in claim 10, wherein the laser output emission and the mutual guiding of each respective focusing device and element take place substantially steplessly or continually on one or both sides of the joint.

* * * * *